United States Patent [19]

Stiso

[11] Patent Number: 4,999,285
[45] Date of Patent: Mar. 12, 1991

[54] CHROMATOGRAPHIC CASSETTE
[75] Inventor: S. Nicholas Stiso, San Jose, Calif.
[73] Assignee: Syntex (U.S.A.) Inc., Palo Alto, Calif.
[21] Appl. No.: 672,568
[22] Filed: Nov. 15, 1984
[51] Int. Cl.⁵ .................. G01N 33/53; G01N 33/558; G01N 30/90; G01N 30/02
[52] U.S. Cl. ..................... 435/7.9; 435/810; 435/7.7; 435/7.91; 435/7.92; 436/162; 436/514; 422/56; 422/58; 422/70; 210/658; 210/198.3; 210/95
[58] Field of Search ................. 422/56, 58, 59, 61, 422/70; 436/161, 162, 514, 515, 165; 435/292, 294, 810, 7; 73/61.1 C; 206/569, 305, 306; 210/658, 198.2, 198.3, 95

[56] References Cited

U.S. PATENT DOCUMENTS

| 3,510,263 | 5/1970 | Hach | 422/56 |
|---|---|---|---|
| 3,620,677 | 11/1971 | Morison . | |
| 3,623,602 | 11/1971 | Valente | 73/61.1 C |
| 4,168,146 | 9/1979 | Grubb et al. . | |
| 4,298,688 | 11/1981 | Kallies | 422/56 |
| 4,361,537 | 11/1982 | Deutsch et al. | 422/56 |
| 4,428,908 | 1/1984 | Ashley et al. . | |
| 4,435,504 | 3/1984 | Zuk et al. . | |
| 4,517,288 | 5/1985 | Giegel et al. | 436/514 |

FOREIGN PATENT DOCUMENTS 1910527 9/1969 Fed. Rep. of Germany ...... 210/658
0872905 7/1961 United Kingdom .
1037867 8/1966 United Kingdom ............ 73/61.1 C Primary Examiner—Randall E. Deck
Attorney, Agent, or Firm—Theodore J. Leitereg; Linda J. Nyari

[57] ABSTRACT

A chromatographic device is disclosed. The device comprises in combination a housing, a strip of bibulous material non-removably confined in the housing. The strip has a length and width only slightly less than the length and width of the inner walls of the housing. The inner walls of the housing have means attached thereto for supportively confining the strip in the housing. The strip is confined so that (1) the front and back of the strip are essentially free from contact with the walls of the housing and (2) the capillary action of the strip remains substantially unchanged, and (3), where the strip is paper, the strip is allowed to expand as it is traversed by the liquid medium. The bottom end of the housing contains means for enabling contact of a portion of the strip with the liquid medium. The housing further contains means for visually observing the strip and can also contain indicating means cooperative therewith to assist in determining the result of a chromatographic test. The present device has particular application in immunochromatography for the determination of the presence of an analyte suspected of being present in a sample.

30 Claims, 2 Drawing Sheets

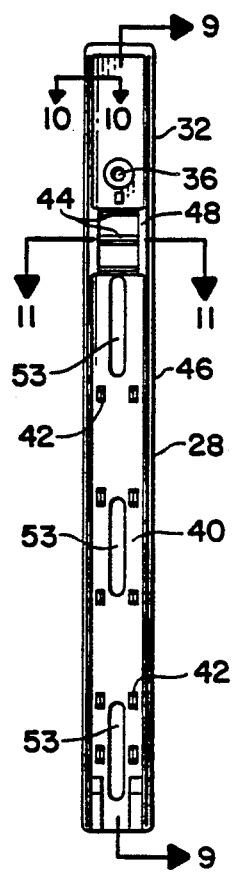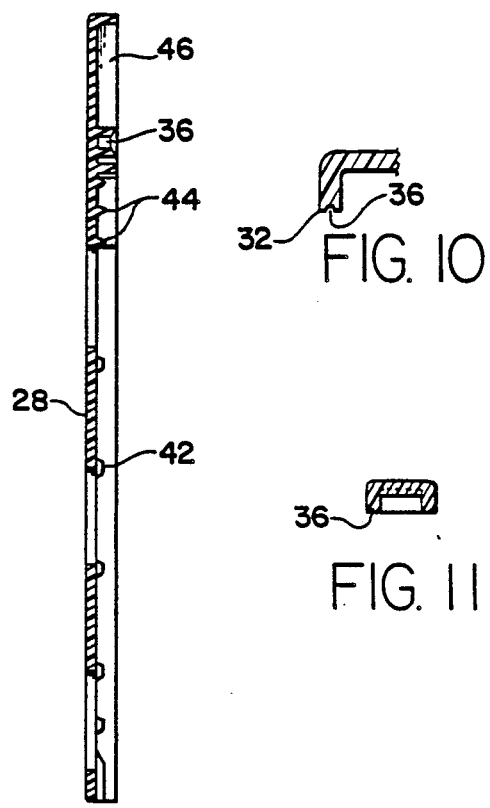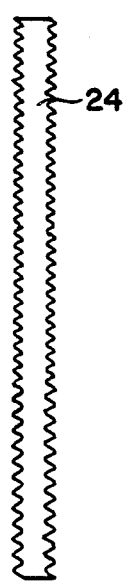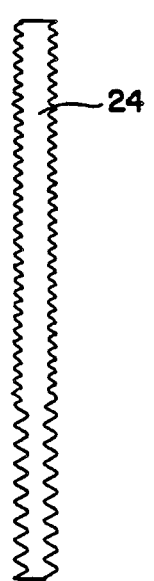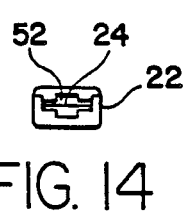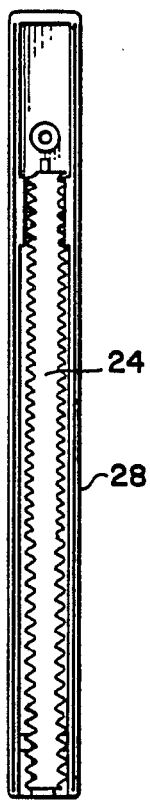

CHROMATOGRAPHIC CASSETTE

BACKGROUND OF THE INVENTION

1. Field of the Invention

The field of competitive protein binding assays or specific binding assays has greatly expanded, as its importance in the diagnostic field has become recognized. The ability to be able to detect a specific compound and measure the compound quantitatively has permitted the monitoring of the administration of a wide variety of drugs, the determination of an imbalance in a wide variety of hormones, the quantitation of physiologically active proteins, and the diagnosis of the presence of a pathogen. The different techniques have been distinguished in requiring or not requiring separation steps, the nature of the signal developed by the label, the development of the signal in a solution or on a surface and the manner of measurement for a quantitative determination.

In developing an assay, there are a number of considerations in devising the reagents and protocol. One consideration is the degree of sophistication of the individual performing the assay. There are many situations where it is desirable to have a relatively untrained individual be able to carry out an assay and obtain reasonably quantitative results. It is particularly desirable that the relatively untrained individual be able to carry out a quantitative assay in a simple, rapid test without the need for sophisticated equipment.

2. Description of the Prior Art

U.S. Pat. No. 4,168,146 describes an immunoassay employing immunochromatography with antigens followed by contacting the immunochromatograph with an aqueous solution containing labelled antibodies. U.S. Pat. No. 4,435,504 discloses a chromatographic immunoassay employing a specific binding pair member in a label conjugate which delineates a border whose distance from one end of the chromatograph relates to the amount of analyte present. An indicator strip useful in analytical chemical procedures is described in U.S. Pat. No. 3,715,192. U.S. Pat. No. 3,620,677 discloses an indicating device comprising in combination a porous capillary material and an impervious covering material enclosing at least a major portion of the exterior surfaces of the capillary material and disposed in intimate contact therewith defining an absorptive cavity of a preselected volume. A method for sonically securing articles in plastic mounts is described in U.S. Pat. No. 4,230,757. A contamination filter mask with a series of discreetly and scientifically oriented cutouts adapted to expose complementary regions of an adjacent filter for visual inspection and for particle count purposes is disclosed in U.S. Pat. No. 3,350,979. U.S. Pat. No. 2,371,405 describes a gas analysis apparatus.

SUMMARY OF THE INVENTION

The present invention is directed to a chromatographic device. The device comprises in combination a housing and a strip of bibulous material non-removably confined in the housing. The strip generally has a length and width only slightly less than the length and width of the inner walls of the housing. The inner walls of the housing contain means for supportively confining the strip in the housing so that (1) the front and back of the strip are essentially free from contact with the walls of the housing and (2) the capillary action of the strip remains substantially unchanged, and (3), where the strip is paper, the strip is allowed to expand as it is traversed by a liquid medium. The bottom end of the housing contains means for enabling contact of a portion of the strip with a liquid medium. The housing further contains means for visually observing the strip and can contain means cooperative therewith for assisting in determining the result of a chromatographic test. The present device is particularly suitable for quantitative determination of the amount of analyte in a sample suspected of containing the analyte. For such use the strip contains one or more reagents reactive with the analyte in a liquid medium traversing the strip by capillary action.

BRIEF DESCRIPTION OF THE DRAWINGS

FIG. 8 is a perspective view, taken from the front, of the rear half of a device in accordance with the present invention.

FIG. 9 is a cross-sectional view of the device of FIG. 8 along lines 9—9.

FIG. 10 is a cross-sectional view of the device of FIG. 8 taken along lines 10—10.

FIG. 11 is a cross-sectional view of the device of FIG. 8 taken along lines 11—11.

FIGS. 12 and 13 are perspective views, taken from the front, of strips which can be confined in the device of the present invention.

FIG. 14 is a perspective view, taken from the bottom, of an opening in the device of FIG. 1.

FIG. 15 is a perspective view, taken from the front, of a partially assembled device in accordance with the present invention.

DESCRIPTION OF THE SPECIFIC EMBODIMENTS

Figure 1:
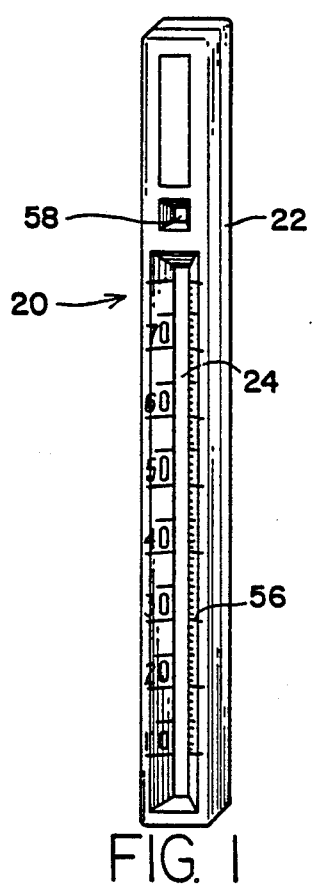
FIG. 1 is a perspective view, taken slightly from the side, of a device in accordance with the present invention.
Figure 2:
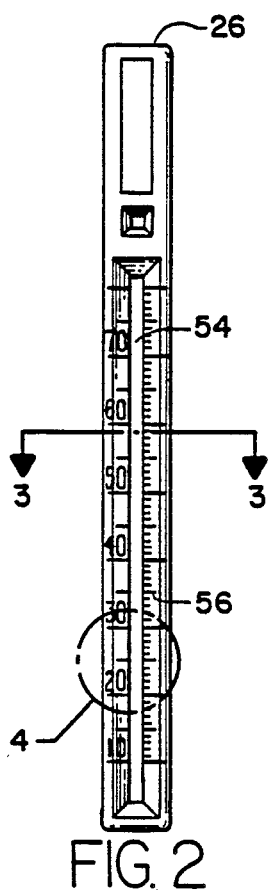
FIG. 2 is a perspective view, taken from the front, of the front half of a device in accordance with the present invention.
Figure 3:
FIG. 3 is a cross-sectional view of the device of FIG. 2 taken along lines 3—3.
Figure 4:
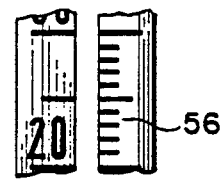
FIG. 4 is a perspective view, taken from the front, of part of a scale on the front half of the device of the invention.
Figure 5:
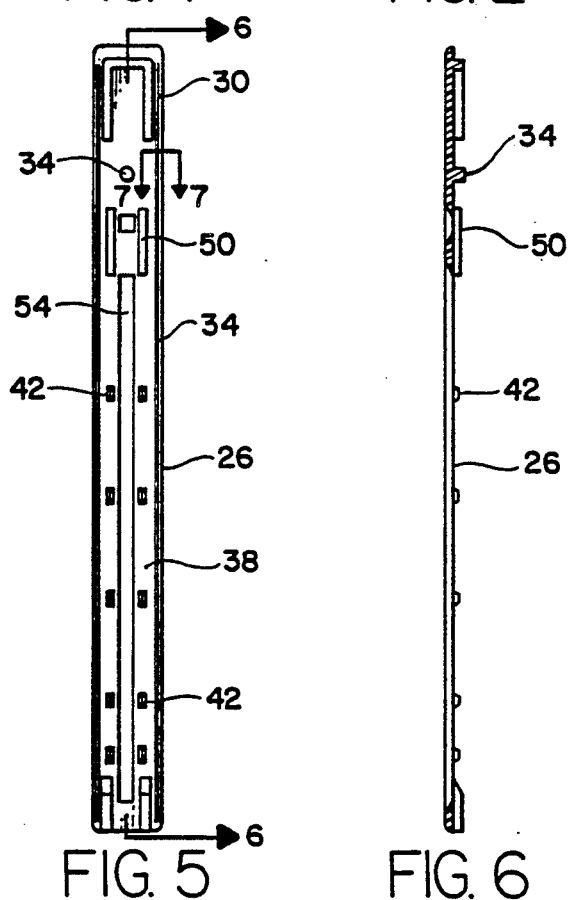
FIG. 5 is a perspective view, taken from the rear, of the front half of the device of the invention.
Figure 6:
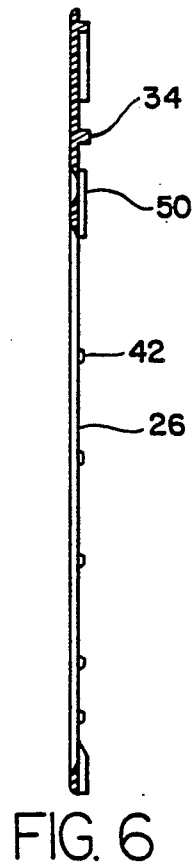
FIG. 6 is a cross-sectional view of the device of FIG. 5 taken along lines 6—6.
Figure 7:
FIG. 7 is a cross-sectional view of the device of FIG. 5 taken along lines 7—7.

The present invention concerns a chromatographic device which has particular application to the quantitative determination of the amount of an analyte in a sample suspected of containing the analyte. The device comprises a housing, usually small, and a strip of bibulous material non-removably confined in the housing. The strip generally has a length and width only slightly less than the length and width of the inner walls of the housing. The inner walls of the housing contain means for supportively confining the strip in the housing. Generally, this means takes the form of a plurality of elements which protrude from the front and rear inner walls of the housing. This means supportively confines the strip in the housing so that (1) the front and back of the strip are essentially free from contact with the walls of the housing and (2) the capillary action of the strip remains substantially unchanged, and (3), where the strip is paper, the strip is allowed to expand as it is traversed by a liquid medium. The bottom end of the housing contains means for enabling a portion of the strip to contact the liquid medium. The housing additionally includes means for visually observing the strip and indicating means cooperative therewith for assisting in determining the result of a chromatographic test.

The strip of bibulous material is usually a paper strip and normally contains reagents for conducting a chemical test, such as, for example, reagents for conducting an assay, preferably an immunoassay. In a preferred embodiment of the present invention, the device further comprises means incorporated into said housing for determining the distance along the strip traversed by the liquid medium.

In the subsequent description of the subject invention the following definitions will be used.

Analyte—The compound or composition to be measured, which may be a ligand, which is mono- or polyepitopic, antigenic or haptenic, a single or plurality of compounds which share at least one common epitopic site or a receptor.

Specific Binding Pair Member ("sbp" member)—Two different molecules, where one of the molecules has an area on the surface or in a cavity which specifically binds to a particular spatial and polar organization of the other molecule. The members of the specific binding pair are referred to as ligand and receptor ("anti-ligand"). For the most part, the receptor will be an antibody and the ligand will serve as an antigen or hapten and to that extent are members of an immunological pair.

Ligand—Any organic compound for which a receptor naturally exists or can be prepared.

Receptor ("Anti-Ligand")—Any compound or composition capable of recognizing a particular spatial and polar organization of a molecule, i.e., epitopic site. Illustrative receptors include naturally occurring receptors, e.g. thyroxin binding globulin, antibodies, enzymes, FAB fragments, lectins and the like.

Label—The label may be any molecule conjugated to another molecule or support and, where two molecules are involved, is arbitrarily chosen as to which molecule is the label. In the subject invention, the labels will be an sbp member which is conjugated to a support or a member of the signal producing system that is conjugated to a support or an sbp member.

Signal Producing System—The signal producing system may have one or more components, at least one component being conjugated to an sbp member. The signal producing system produces a measurable signal which is detectable by external means, normally by measurement of the electromagnetic radiation, desirably by visual examination. For the most part, the signal producing system involves chromophores and enzymes, where chromophores include dyes which absorb light in the ultraviolet or visible region, phosphors, fluorescers and chemiluminescers.

Immunochromatograph—The immunochromatograph has a plurality of sbp members, either ligand or receptor, bound in an region to a bibulous support which allows for the movement of a liquid across the region with transport of the analyte and, as appropriate, any members of the signal producing system. The sbp members are non-diffusively bound to the support, either covalently or non-covalently. In addition, one or more members of the signal producing system may be non-diffusively bound to the bibulous support, either covalently or non-covalently.

The device of the present invention will now be described in greater detail with reference to the attached drawings, which are provided for purposes of illustration and not meant to be a limitation on the scope of the present invention.

Chromatographic device 20 in FIG. 1 has housing 22 which may be formed conveniently of a thermoplastic material, or the like. The device generally has dimension of about 10 to 14 cm in length, 8 to 12 mm in width, and about 4 to 6 mm in depth. A strip of bibulous material 24 is non-removably confined in the housing. The strip has a length and width only slightly less than the length and width of the inner walls of the housing. Preferably the strip of bibulous material is a paper strip, more preferably an immunochromatograph.

A preferred embodiment for assembling the chromatographic device of the present invention may be seen with reference to FIGS. 2-15. The present device is conveniently formed from two pieces herein referred to as front piece or half 26 and back piece or half 28. Pieces 26 and 28 are joined along edge lines 30 on piece 26 and 32 on piece 28. Conveniently, the two halves can include means for interlocking the halves. For example, front half 26 can contain protrusion 34 which is designed to snap fit with protrusion receiving means 36. After placing strip 24 in piece 28 (FIG. 15), piece 26 and piece 28 are joined together along their edges and 34 is snap fit into 36. Piece 26 and piece 28 may be sealed together to produce housing 22 by application of sonic energy, an adhesive, heat, or the like, according to conventional techniques. The preferred technique is the application of sonic energy to produce a sonic weld and the edge can be equipped with appropriate energy directors. The use of front and back pieces for assembling the device of the invention is merely illustrative. Other means of forming the present device will be suggested to those skilled in the art to having reference to the disclosure contained herein.

The inner walls of housing 22 contain means for supportively confining strip 24 in the housing so that certain results are realized. These results are: (1) the front and back sides of strip 24 are essentially free from contact with the inner walls 38 and 40 of housing 22, and (2) the capillary action of the strip remains substantially unchanged, and (3), where the strip is paper, the strip is allowed to expand as it is traversed by a liquid medium. The above identified results are extremely important to the successful operation of the chromatographic device of the present invention. As mentioned above, the strip has a length and a width only slightly less than the length and width of the inner walls 38 and 40 of housing 22. The successful operation of the device is dependent upon having a strip of bibulous material of sufficient size to carry out a chemical test and obtain an accurate result. Thus, the strip of bibulous material cannot be too small such that sensitivity is lost. On the other hand, the strip cannot be so large as to require that the chromatographic device have large dimensions. The device should be easily manipulated by the fingers of one hand. Furthermore, the strip must be free from contact with the inner walls of the housing so that the capillary action of the strip is unimpaired. If the strip is allowed to touch the inner walls of the housing, the capillary action of the bibulous strip can be impaired and produce an erroneous result during an assay. Additionally, as a liquid medium traverses the strip by capillary action, the dry strip becomes wet and expands. Thus, the means attached to the inner walls of the housing for supportively confining the strip must be such as to allow the strip to expand without allowing the strip to contact the inner walls of the housing.

Exemplary of such means are protruding elements 42 found on inner walls 38 and 40 of housing 42. Elements 42 are generally integral with the inner walls of housing 22 and may be in the form of posts which are conical, oblong, oval, rectangular, triangular, or the like. A key feature of elements 42 is that they minimize the contact area with strip 24 so that the capillarity of strip 24 is not altered in any significant manner. By the term "altering in any significant manner" is meant that the capillary action of strip 24 is not altered such that the performance of the chemical test is significantly affected thereby reducing or eliminating the accuracy of the test. For example, where strip 24 is an immunochromatograph sufficient capillary action must be maintained in order to be able to accurately quantitate the amount of analyte in a sample. In general, elements 42 lie in rows parallel to the longitudinal sides of housing 22. Generally, elements 42 have dimensions such as to allow slight forward and rearward movement of the strip in the housing in the dry state and to prevent such movement when the strip is wetted by the traversing liquid. Usually, the distance of forward to rearward movement is 0.5 mm to 1.0 mm when the strip is in the dry state. Generally, on each of the front and rear inner walls of housing 22, there are about from 4 to 6 elements per side, having a length of about 2 to 4 mm.

Usually strip 24 is secured in housing 22 at the upper or distal end of strip 24 (FIG. 15). Accordingly, front and rear walls 26 and 28 of housing 22 are equipped with means for securing the top portion of strip 24 in housing 22. Such means may include, for example, ridges forming an integral part of walls 26 and 28, which ridges run transverse to the side walls of housing 22. These ridges provide intimate contact with the upper portion of strip 24 and secure strip 24 within housing 22. Referring to FIGS. 8 and 9, rear wall 28 contains triangular shaped ridges 44 which form an integral part of rear wall 28. Ridges 44 run transverse to side walls 46 of housing 22. At the portion where strip 24 is secured in housing 22, side walls 46 narrow such that intimate contact is made between the sides of strip 24 and the narrowed portion 48 of housing 22 to assist in securing strip 24 in housing 22. Front wall 26 is provided with protruding ridges 50 running parallel to the side walls of housing 22. Ridges 50 are of sufficient size to provide intimate contact with strip 24 so that strip 24 is secured between ridges 44 and 50.

The present chromatographic device also includes means incorporated into the bottom end of housing 22 for enabling contact of a portion of strip 24 with a liquid medium. Referring to FIG. 14, housing 22 contains an opening 52 at the bottom of housing 22. This opening provides a dual function. It allows liquid medium to contact strip 24 and also allows the device to drain together with openings 53 in back wall 28.

The chromatographic device of the invention further includes means incorporated in housing 22 for visually observing strip 24. Referring to the attached drawings, such means is provided by opening 54 in front wall 26 of housing 22. Opening 54 generally runs parallel to the side walls of housing 22. The length of opening 54 is determined by the chemical test which is being conducted using the present chromatographic device. For the most part, where strip 24 is an immunochromatograph, the length of opening 54 will allow a substantial portion, greater than 50%, preferably greater than 80% of the surface of strip 24 to be visualized.

The present device further includes indicating means cooperative with the means for visually observing the strip. The indicating means assists in determining the result of a chromatographic test. Referring to the attached drawings, the indicating means may take the form of graduated scale 56. In the situation where strip 24 is an immunochromatograph, the graduations of scale 56 can be related to a certain analyte concentration in an unknown sample.

The present device further comprises means incorporated into housing 22 for determining the distance along strip 24 traversed by a liquid medium. Front wall 26 of housing 22 contains, at its upper or distal end, opening 58 for visualizing the upper portion of strip 24. The upper portion of strip 24 can contain a conventional water soluble dye just below opening 58. An aqueous medium traversing strip 24 contacts the dye and transports it into view through opening 58. Alternately, the portion of strip 24 that is viewed through opening 58 can contain an agent which has one color in the dry state and another in the wet state such as cobalt chloride, copper chloride, and the like. Another embodiment can have a pH indicator on the portion of strip 24 viewed through opening 58. The pH indicator can exhibit a color at the pH of the traversing medium different from the color in the dry state. Alternatively, the upper portion of strip 24 can contain a chemical agent, such as, for example, a dye, a dye precursor, an enzyme, an enzyme substrate, or the like, which upon contact with the liquid medium produces a signal which may be visualized through opening 58.

As mentioned above, the device of the present invention can be employed to determine the result of a chemical test particularly by employing a chromatographic step. The present device finds particular application in a method for determining quantitatively the amount of an analyte in a sample suspected of containing the analyte. In this preferred use, strip 24 is an immunochromatograph. Examples of such immunochromatograph and method of using the immunochromatograph are described in U.S. Pat. Nos. 4,168,146 and 4,435,504, the disclosures of which are incorporated herein by reference.

The known immunochromatographic method is carried out on a bibulous strip, e.g., step, involving a stationary solid phase and a moving liquid phase. The stationary solid phase can be contacted with a plurality of reagents in a number of different solutions.

The region in which the sbp member is non-diffusively bound to the bibulous strip is referred to as the "immunosorbing zone". The analyte from the sample will traverse this zone being carried along with a solvent whose front crosses the zone. The analyte, which is the homologous or reciprocal sbp member to the sbp member bound to the support, becomes bound to the support through the intermediacy of sbp member complex formation. The signal producing system provides the manner by which the area in the immunosorbing zone to which the analyte is bound may be distinguished from the area in which it is absent, so that the distance from a predetermined point on the immunochromatograph is a measure of the amount of analyte in the sample.

The incremental movement of the sample through the immunosorbing zone results from dissolving the sample in an appropriate solvent and the transport of the solution through the immunosorbing zone due to capillarity.

The solvent will normally be an aqueous medium, which may be up to about 40 weight percent of other polar solvents, particularly oxygenated solvents of from 1 to 6, more usually of from 1 to 4 carbon atoms, including alcohols, ethers and the like. Usually, the cosolvents will be present in less than about 20 weight percent.

The pH for the medium will usually be in the range of 4–11, more usually 5–10, and preferably in the range of about 6.5–9.5. The pH is chosen to maintain a significant level of binding affinity of the sbp members. Various buffers may be used to achieve the desired pH and maintain the pH during the elution. Illustrative buffers include borate, phosphate, carbonate, tris, barbital and the like. The particular buffer employed is not critical, but in individual assays, one buffer may be preferred over another.

Desirably, from about 0.05 to 0.5 wt. % of a non-ionic detergent is included with the sample. Various polyoxyalkylene compounds may be employed of from about 200 to 20,000 daltons.

Moderate, and desirably substantially constant, temperatures are normally employed for carrying out the assay. The temperatures for the chromotography and production of a detectable signal will generally be in the range of about 10°–50° C., more usually in the range of about 15°–50° C., and frequently will be ambient temperatures, that is, about 15°–25° C.

The concentration of analyte which may be assayed will generally vary from about $10^{-4}$ to about $10^{-15}$M, more usually from about $10^{-6}$ to $10^{-14}$M. Considerations, such as the concentration of the analyte of interest and the protocol will normally determine the concentration of the other reagents.

While the concentrations of many of the various reagents in the sample and reagent solutions will generally be determined by the concentration range of interest of the analyte, the final concentration of each of the reagents will normally be determined empirically to optimize the sensitivity of the assay over the range of interest. However, with certain protocols, individual reagents may be used in substantial excess without detrimentally affecting the sensitivity of the assay.

The size of the immunosorbing zone need have no upper limit, except for practical considerations as mentioned earlier. Since, for the most part, low concentrations are being assayed, the width of the immunoabsorbing zone will tend to be relatively narrow, so that the analyte may traverse a reasonable distance and provide for reasonable differentiation over the concentration range of interest. Generally, the width of the strip will not be less than about 0.2 mm and not more than about 2 cm, generally ranging from about 5 mm to 20 mm, preferably from about 5 mm to 15 mm.

The length of the immunoabsorbing zone will be desirably at least about 2 to 10 times the width, usually at least about 2 mm, more usually at least about 10 mm, preferably at least about 23 mm, and not more than about 12 cm, usually not more than about 10 cm, preferably from about 5 to 10 cm. The distance traversed is a factor in the time required for the assay, which will be taken into account with the other factors affecting the time required for the assay.

Other reagents which are members of the signal producing system may vary widely in concentration depending upon the particular protocol and their role in signal production. In a "true" competitive situation between a labeled sbp member and the analyte, usually the labeled sbp member will not exceed 10 times the maximum concentration of interest of the analyte and will not be less than about 0.5 times the minimum concentration of interest. In most other situations, the amount of the other reagents involved in sbp member complex formation may be present in an amount substantially less than the binding equivalent of analyte or in substantial excess to the binding equivalent of analyte. Therefore, no simple relationship can be provided.

In carrying out the assay, the protocol will normally involve dissolving the sample into the eluting solvent. The sample may be derived from a wide variety of sources, such as physiologic fluids, illustrated by blood, serum, plasma, urine, ocular lens fluid, spinal fluid, etc., chemical processing streams, food, pesticides, pollutants, etc.

The bottom or proximal end of device 20 (i.e., the end of device 20 that is contacted with the liquid medium) will then be contacted with the sample dispersed in the solvent, which will normally be a buffered aqueous medium which may contain one or more members of the signal producing system. Where a member of the signal producing system is present, at least one member will be conjugated to a sbp member to provide a sbp member-label conjugate.

Sufficient time will be allowed for the solvent front to complete traversal of the immunosorbing zone which can be determined by viewing opening 58. The zone has sufficient sbp member to insure that all of the analyte becomes bound in said zone without exhausting the sbp member bound in the zone.

Where the immunochromatograph is not standardized to the extent that variations in conditions may change the distance the analyte traverses, a standard sample can be provided having a known amount of analyte. The analyte sample and the standard can be run at the same time, and a quantitative comparison can be made between the standard sample and the analyte sample. If necessary, more than one standard can be employed, so that the distance traversed can be graphed for the different concentrations and used to quantitate a particular sample.

For the most part, relatively short times are involved for the immunochromatograph. Usually, the traverse of the sample through the immunosorbing zone will take at least 30 sec and not more than 1 hour, more usually from about 1 min to 30 min. The development of the signal will generally range from 30 sec to 30 min, more usually from about 30 sec. to 5 min.

The signal producing system has at least one enzyme and may have two or more other components of the signal producing system or one or more substrates, and may also include coenzymes. Any member of the signal producing system may be employed as a label, where the presence of the label on the immunochromatograph provides for a substantial change in signal in the area of the label. Therefore, labels may include enzymes or coenzymes, but not substrates. Usually, the label will be an enzyme.

The individual or combination of enzyme labels may be varied widely. The product producing the detectable signal may be a dye, fluorescer or chemiluminescer, with the signal detected by visual observation, due to absorption, fluorescence, or chemiluminescence, or a spectrophotometric measurement, employing measuring absorption, reflectance, fluorescence or chemiluminescence.

For the most part the enzymes of interest will be oxidoreductases and hydrolases. A large number of enzymes of interest are set forth in U.S. Pat. No. 4,275,149 the relevant portion of which is incorporated herein by reference. For combinations of enzymes one enzyme is non-diffusively bound to the immunochromatograph, while the other enzyme is conjugated to a sbp member.

After the sample has traversed the immunosorbing zone, if the label-sbp member conjugate was not combined with the sample, the immunosorbing zone is contacted substantially uniformly with a solution having labeled-sbp member conjugate and depending on the label and protocol one or more other members of the signal producing system.

In the case of an enzyme-sbp member conjugate the immunosorbing zone is contacted with a solution of enzyme-sbp member conjugate and substrate, optionally with a scavenger. In this situation an enzyme is bound to the immunochromatograph in the immunosorbing zone,, which is related to the enzyme bound to the sbp member, by the substrate of one being the product of the other. The enzyme-sbp member conjugate will normally be in an aqueous buffered solution and may be present in substantial excess of available binding sites. The pH range and buffers have been previously considered. After a sufficient time for the enzyme-sbp member conjugate to bind either to ligand or receptor, and for color to form, the immunochromatograph is removed from the solution.

By having the two enzymes, a step in the protocol is eliminated since the enzyme-sbp member conjugate and substrate may be combined in the same solution without reaction prior to contacting the immunosorbing zone.

After the enzyme-sbp member conjugate is bound to the immunochromatograph by being present in the sample, the immunchromatograph is developed by immersion in a substrate solution. In this case an enzyme may or may not be bound to the immunochromatograph.

With the conenzyme label, the developer solution will usually contain one or more enzymes to provide for regeneration of the coenzyme and substrate. Since the enzymatic reaction requires the coenzyme, the enzyme and substrate may be combined as a single developer reagent without any reaction prior to contact with the immunsorbing zone.

The substrates will vary with the enzymes and are normally in substantial excess, so as not to be rate limiting (greater concentration than Km). The aqueous solution will usually be appropriately buffered for the enzyme system and may include a scavenger for the product of the enzyme which is the substrate of the other enzyme, e.g., catalase for hydrogen peroxide from uricase.

The chromatographic device is contacted with the developer solution for a sufficient time to produce sufficient detectable signal producing compound so as to define the region of the immunosorbing zone in which the analyte is bound. Once the detectable signal has been produced, the distance from one end of the chromatograph may be measured as a quantitative measure of the amount of analyte in the sample by employing indicating means 56.

While some distortion may be observed at the border, in most situations the border is reasonable well defined, so that changes in concentration of factors of two or less in the $\mu$g to pg range can be detected with a wide variety of analytes. Thus, by employing an appropriate d precursor as a substrate, the amount of an analyte can be quantitatively determined by visual observation with a single measurement (the sample) by the user and a two-step protocol which is relatively insensitive to interference.

The ligand analytes are characterized by being monoepitopic or polyepitopic, while the receptor analytes may have a single or plurality of binding sites. The polyepitopic analytes will normally be poly(amino acids), i.e., polypeptides and proteins, polysaccharides, nucleic acids, and combinations thereof. Such combinations or assemblages include bacteria, viruses, chromosomes, genes, mitochondria, nuclei, cell membranes and the like.

For the most part, the polyepitopic ligand analytes will have a molecular weight of at least about 5,000, or usually at least about 10,000. In the poly(amino acid) category, the poly(amino acids) of interest will generally be from about 5,000 to 5,000,000 molecular weight, more usually from about 20,000 to 1,000,000 molecular weight, and among hormones of interest, about 5,000 to 60,000 molecular weight.

An extensive listing of useful ligands may be found in U.S. Pat. No. 4,275,149, the disclosure bridging columns 12 to 17, which disclosure is incorporated herein by reference.

The monoepitopic ligand analytes will generally be from about 100 to 2,000 molecular weight, more usually from about 125 to 1,000 molecular weight. The analytes of interest include drugs, metabolites, pesticides, pollutants, and the like.

A large number of analytes of interest are listed in U.S. Pat. No. 4,275,149, columns 17 and 18, which disclosure is incorporated herein by reference.

For receptor analytes, the molecular weights will generally range from about $10^4$ to $2 \times 10^8$, more usually from about $3 \times 10^4$ to $2 \times 10^6$. For immunoglobulins, e.g., IgA, IgD, IgE, IgG and IgM, the molecular weights will generally vary from about 160,000 to about $10^6$. Enzymes will normally vary from about 10,000 to 600,000 daltons. Natural receptors vary widely, being generally at least about 25,000 molecular weight and may be $10^6$ and higher, including such materials as avidin, thyroxine binding globulin, thyroxine binding prealbumin, transcortin, membrane surface proteins, etc.

Where a ligand is conjugated to another molecule or support, frequently the ligand will be modified to provide for a particular functional group at a particular site. This modification produces a product referred to as a ligand analog. U.S. Pat. No. 4,275,149 also has an extensive description of ligand analogs, bridging columns 18 and 19, which description is incorporated herein by reference.

The immunochromatograph involves a bibulous support providing liquid travel through capillarity, a non-diffusively bound sbp member, and may also include one or more members of the signal producing system.

A wide variety of bibulous materials may be used for the strip which include both natural and synthetic polymeric materials, particular cellulosic materials, such as fiber containing papers, e.g., filter paper, chromatographic paper, etc., synthetic or modified natural occuring polymers, such as poly(vinyl chloride), cross-linked dextran, acrylates, etc., either used by themselves or in conjuction with a ceramic material, such as silica.

The thickness of the immunchromatograph bibulous support will generally vary from about 0.05 mm to about 2 mm, more usually being about 0.1 mm to 0.5 mm, preferably from about 0.2 mm to about 0.4 mm. The structure can be varied widely and includes fine, medium fine, medium, medium coarse and coarse. The surface can be varied widely with varying combinations of smoothness and roughness combined with hardness and softness.

The immunochromatograph can be supported by a variety of inert supports, such as Mylar, polystyrene, polyethylene, or the like. The supports can be used as a backing spaced from the immunochromatograph, edging, or other structure to enhance the mechanical integrity of the immunochromatograph.

The immunochromatograph can be coated with a wide variety of materials to provide for enhanced properties. Coatings may include protein coatings, polysaccharide coatings, sugars or the like, which are used particularly to enhance the stability of the materials conjugated to the support. These compounds can also be used for improved binding of the materials, such as the sbp member or signal producing system member bound to the immunochromatograph.

The immunochromatograph can be activated with reactive functionalities to provide for covalent bonding of the organic materials to be conjugated to the support-such as those described in U.S. Pat. No. 4,168,146.

The amount of sbp member which is bound to the support will vary depending upon the size of the support and the amount required to bind all of the analyte and, as required, labeled sbp member. Generally, the amount of sbp member will range from about $10^{-5}$ to $10^{-14}$ moles/cm$^2$, more usually from about $10^{-7}$ to $10^{-12}$ moles/cm$^2$. The number of moles per unit area will be varied in order to insure that there is sufficient discrimination in the concentration range of interest for the distance traversed by the analyte.

In a preferred embodiment, a signal producing system member is non-diffusively bound to the bibulous support. Particularly, an enzyme is bound to the support which will interact with the labeled sbp member, where the label is another enzyme. The relationship of the enzymes will be discussed in the description of the signal producing system.

Both the sbp member and the signal producing system member may be bound to a variety of supports by adsorption, rather than covalent bonding. This will involve contacting the bibulous support with the solution containing the sbp member and/or signal producing member, removing the immunochromatograph from the solution, and allowing the immunochromatograph to dry. Alternatively, the solution may be applied by spraying, painting, or other technique which will provide uniformity.

Generally, relatively large sheets will be used which can then be cut to the appropriate dimensions. The edges of strips 24 can be modified to control the shape of the front of the traversing component. Such modification includes serration and chemical treatment of the edges as described in U.S. Ser. No. 591,155, filed Mar. 16, 1984, the disclosure of which is incorporated herein by reference. The edges of strips 24 can also be cut by non-compressive means such as by laser means as disclosed in U.S. Ser. No. 599,386, filed Apr. 12, 1984, the disclosure of which is incorporated herein by reference.

The signal producing system will, for the most part, involve the production of a detectable signal involving the absorption or emission of electromagnetic radiation, particularly light in the ultraviolet and visible region, more particularly radiation having a wavelength in the range of about 400 to 800 nm. Because of the nature of the immunochromatograph, in order to have a detectable signal, it is necessary that there be a sufficient concentration of the label over a unit area. Therefore, for the most part, individual labels will not be sufficient to provide the desired sensitivity. To that extent, means must be provided for the generation of a plurality of detectable molecules associated with a single labeled sbp member, where the label which provides the means for such generation does not interfere with the traversing of the labeled sbp member, when the labeled sbp member traverses the immunosorbing zone. Therefore, one employs a label which produces a large number of molecules which can be detected, such as an enzyme or coenzyme. Amplification is then obtained by the presence of a single label.

An enzyme or coenzyme is employed which provides the desired amplification by producing a product, which absorbs light, e.g., a dye, or emits light upon irradiation or chemical reaction, a fluorescer, or chemiluminescer. A large number of enzymes and coenzymes for providing such products are indicated in U.S. Pat. No. 4,275,149 bridging columns 19 to 23, and U.S. Pat. No. 4,318,980, columns 10 to 14, which disclosures are incorporated herein by reference.

Of particular interest is the use of a combination of enzymes, where the enzymes are related by the product of one enzyme being the substrate of the other enzyme. In this manner, non-specific interference is substantially reduced and the border between the zones containing the bound analyte and free of analyte is more effectively defined.

A number of enzyme combinations are set forth in U.S. Pat. No. 4,275,149, bridging columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, e.g., peroxidase, microperoxidase, and cytochrome C oxidase. Additional enzyme combinations may be found in the subject matter incorporated by reference. While the above oxidoreductase combination is preferred, other enzymes may also find use such as hydrolases, transferases, and oxidoreductases other than the ones indicated above.

Illustrative coenzymes which find use include NAD[H]; NADP[H], pyndixal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

By appropriate manipulation or choice of the label-sbp member conjugate, the receptors, the bibulous support and the conditions employed in performing the assay, two different embodiments of the subject invention can be achieved where the analyte and enzyme-sbp member are applied to the immunochromatograph in the same solution. In one embodiment, the region of the immunosorbing zone traversed by the analyte is observable due to production of the detectable signal substantially uniformly throughtout the region in which the analyte is present. In the other embodiment, the detectable signal is primarily observable at a border related to the region in the immunsorbing zone occupied by the analyte.

The different results may be related to different binding constants, rates of travel, adsorption or the like, of the label-sbp member conjugate as compared to the analyte. The variations can be achieved by varying the number of sbp members, particularly haptenic analytes, bound to the labels, varying the binding specificity of receptors bound to the bibulous support, e.g., by preparing antibodies to an immunogen having one linking group between the hapten analyte and antigen and employing a different linking group with the label-hapten analyte conjugate, varying the solvent and/or support to vary the Rf factors, or other techniques.

As a result of the use of two enzymes in the signal producing system with one enzyme as a label, a simplified protocol can be employed, also a strong detectable signal is obtained providing for accurate delineation of the front to which the analyte progressed. By having the product of the enzyme bound to the bibulous support be the substrate of the enzyme conjugated to the sbp member, a sharp, rapid and uniform development of the detectable signal is observed on the immunochromatograph. Furthermore, one establishes a high localized concentration of substrate for the enzyme bound to the immunochromatograph, so as to encourage the rapid deposit of the detectable signal producing compound at the surface.

As a matter of convenience, the present chromatographic device can be provided in a kit in packaged combination with reagents in predetermined amounts for use in assaying for an analyte. Where two enzymes are involved, the reagents will include enzyme labeled sbp member, substrate for the enzyme bound to the immunochromatograph, any additional substrates and cofactors required by the enzymes, and the dye precursor, which provides the detectable chromophore or fluorophore. In addition, other additives may be included, such as stabilizers, buffers, and the like. The relative amounts of the various reagents may be varied widely, to provide for concentrations in solution of the reagents which substantially optimize the sensitivity of the assay. Particularly, the reagents may be provided as dry powders, usually lyophilized, including excipients, which on dissolution will provide for a reagent solution having the appropriate concentrations for combining with the sample.

Although the foregoing invention has been described in some detail by way of illustration and example for the purposes of clarity and understanding, it will be obvious that certain changes or modifications may be practiced within the scope of the appended claims.

What is claimed is:

1. A chromatographic device, comprising in combination
   (a) a housing having front, rear, and inner walls, and top and bottom ends,
   (b) a strip of bibulous material non-removably confined in said housing,
   (c) means attached to the inner walls of said housing for supportively confining said strip in said housing and constructed so as to keep (1) the front and back of said strip free from contact with the inner walls of said housing and (2) the capillary action of said strip substantially unchanged,
   (d) means at the bottom end of said housing for enabling contact of a portion of said strip with a liquid medium, and
   (e) means in the front wall of said housing for visually observing said strip.

2. The device of claim 1 which further includes indicating means corresponding to said means in the front wall of said housing for visually observing said strip for the result of a chromatographic test.

3. The device of claim 1 wherein the means for supportively confining said strip in said housing is further constructed so as to allow the strip to expand as it is traversed by a liquid medium.

4. The device of claim 1 wherein said means for supportively confining said strip in said housing includes protruding elements attached to the front and rear walls of said housing.

5. The device of claim 1 wherein said housing contains means for draining said device.

6. The device of claim 1 wherein said strip of bibulous material is a paper strip.

7. The device of claim 1 wherein said strip of bibulous material contains reagents for conducting a chemical test.

8. The device of claim 1 wherein said strip of bibulous material contains reagents for conducting an assay.

9. The device of claim 1 wherein said strip of bibulous material contains reagents for conducting an immunoassay.

10. The device of claim 9 wherein said reagents for conducting an immunoassay include a plurality of a specific binding pair member.

11. The device of claim 10 wherein said reagents for conducting an immunoassay further include an enzyme.

12. The device of claim 1 wherein said housing is formed from a thermoplastic material.

13. The device of claim 1 which further comprises means in said housing for determining the distance along said strip traversed by the liquid medium.

14. A device for determining quantitatively the amount of an analyte in a sample suspected of containing the analyte, comprising in combination
   (a) a paper strip containing one or more reagents reactive with the analyte in a liquid medium traversing said strip by capillary action wherein the distance along said strip traversed by the analyte is related to the amount of the analyte in the sample,
   (b) a housing enclosing said strip, said housing having front, rear, and inner walls and proximal and distal ends, wherein said strip has a length and width only slightly less than the length and width of the inner walls of said housing so as to allow expansion of said strip as it is traversed by a liquid medium without said strip touching the inner walls of said housing,
   (c) means attached to said housing for supportively confining said strip in said housing and constructed so as to allow (1) the sides of said strip to be free from contact with the inner walls of said housing, (2) the strip to expand as it is traversed by the liquid medium, and (3) the capillary action of said strip to remain substantially unchanged, (d) means in the front wall of said housing for visually observing said strip, (e) indicating means, corresponding to said means for visually observing said strip, for relating the distance traversed by the analyte along said strip to the amount of analyte in said sample, (f) means at the proximal end of said housing for enabling a portion of said strip to contact the liquid medium, and (g) means in said housing for determining the distance along said strip traversed by the liquid medium.

15. The device of claim 14 wherein said housing has the outside dimensions of between about 10 to 14 cm in length, about 8 to 12 mm in width, and about 4 to 6 mm in depth.

16. The device of claim 14 wherein said means for supportively confining said strip in said housing includes a plurality of protruding elements attached to the inner walls of said housing, said elements having dimensions such as to allow slight forward and rearward movement of said strip before said strip is traversed by a liquid medium and to prevent such forward and rearward movement of said strip after said strip is traversed by a liquid medium.

17. The device of claim 14 wherein said means for supportively confining said strip in said housing includes a plurality of protruding elements attached to the inner walls of the distal end of said housing, said elements fixedly securing the distal end of said strip.

18. The device of claim 14 wherein the housing contains means for draining said device.

19. The device of claim 14 wherein the reagents active with the analyte include a specific binding partner for the analyte.

20. The device of claim 14 wherein said paper strip further contains an enzyme.

21. The device of claim 14 wherein said housing is formed from a thermoplastic material.

22. The device of claim 14 wherein said means for determining the distance along said strip traversed by the liquid medium includes an opening on the front wall of said housing for visualizing the distal end of said strip, said distal end containing reagents reactive with said liquid medium to produce a visual signal.

23. A device for determining quantitatively the amount of analyte in a sample suspected of containing the analyte, comprising in combination.

a paper strip containing one or more reagents reactive with the analyte in a liquid medium traversing said strip by capillary action wherein the distance along said strip traversed by the analyte is related to the amount of analyte in the sample, a housing, having front, rear, and inner walls, and top and bottom ends, non-removably enclosing said strip and having a length of from about 10 to 14 cm, a width of from about 8 to 12 mm, and a depth of about 4 to 6 mm, a longitudinal opening along the front wall of said housing for visualizing a portion of said strip, a scale on the front wall of said housing corresponding to said longitudinal opening for determining the distance traversed by the analyte along said strip, a second opening in the bottom end of said housing to permit contact between said strip and a liquid medium and further to permit draining of said device, a third opening on the front wall of the top end of said housing for visualizing a portion of the upper end of said strip, a plurality of protruding elements fixedly attached to the front and rear inner walls of said housing for supporting said strip in said housing so as to allow (1) the sides of said strip to be free from contact with the inner walls of said housing, (2) the strip to expand as it is traversed by a liquid medium, and (3) the capillary action of said strip to remain substantially unchanged.

24. In a method for determining quantitatively the amount of analyte in a sample suspected of containing said analyte, the improvement comprising employing the device of claim 1.

25. In a method for determining quantitatively the amount of analyte in a sample suspected of containing said analyte, the improvement comprising employing the device of claim 14.

26. In a method for determining quantitatively the amount of analyte in a sample suspected of containing said analyte, the improvement comprising employing the device of claim 23.

27. A method for determining quantitatively the amount of analyte in a sample suspected of containing said analyte, comprising
(a) contacting a sample suspected of containing an analyte in a liquid medium with a portion of the device of claim 14,
(b) allowing said liquid medium to traverse at least a portion of said device so as to allow quantitation of said analyte,
(c) reading said indicating means to obtain the distance traversed by the analyte along said strip, and
(d) relating the distance traversed by the analyte along said strip to the amount of analyte in said sample.

28. A method for determining quantitatively the amount of analyte in a sample suspected of containing said analyte, comprising
(a) contacting a sample suspected of containing an analyte in a liquid medium with a portion of the device of claim 24,
(b) allowing said liquid medium to traverse at least a portion of said device so as to allow quantitation of said analyte,
(c) reading said scale to obtain the distance traversed by the analyte along said strip, and
(d) relating the distance traversed by the analyte along said strip to the amount of analyte in said sample.

29. A kit, comprising in packaged combination:
(a) the device of claim 1 and
(b) reagents in predetermined amounts for conducting an assay for an analyte.

30. The kit of claim 29 wherein said reagents include:
an enzyme labeled specific binding pair (sbp) member,
a substrate specific for said enzyme packaged to prevent reaction thereof with said enzyme labeled sbp member prior to said assay, and
a dye precursor.

* * * * *